United States Patent [19]

Slocum et al.

[11] Patent Number: 4,543,953
[45] Date of Patent: Oct. 1, 1985

[54] ANALOG TELEMETRY SYSTEM FOR BIOMEDICAL IMPLANT

[75] Inventors: Chester D. Slocum; Vincent T. Cutolo, both of Miami, Fla.

[73] Assignee: Cordis Corporation, Miami, Fla.

[21] Appl. No.: 514,514

[22] Filed: Jul. 18, 1983

[51] Int. Cl.[4] .............................................. A61B 5/00
[52] U.S. Cl. ............................ 128/419 PT; 128/903; 340/870.31
[58] Field of Search ....... 128/419 P, 419 PS, 419 PT, 128/419 PG, 631, 903; 340/870.1, 870.31

[56] References Cited

U.S. PATENT DOCUMENTS

| | | | |
|---|---|---|---|
| 3,253,588 | 5/1966 | Vuilleumier et al. | 128/903 |
| 3,713,124 | 1/1973 | Durland et al. | 340/870.31 |
| 3,893,111 | 7/1975 | Cotter | 128/631 |
| 3,942,535 | 3/1976 | Schulman | 128/419 PS |
| 4,223,679 | 9/1980 | Schulman et al. | 128/419 PT |
| 4,231,027 | 10/1980 | Mann et al. | 128/419 PT |
| 4,281,664 | 8/1981 | Duggan | 128/419 PT |
| 4,361,153 | 11/1982 | Slocum et al. | 128/419 P |
| 4,416,283 | 11/1983 | Slocum | 128/419 PG |
| 4,450,431 | 5/1984 | Hochstein | 340/870.31 |

*Primary Examiner*—William E. Kamm
*Assistant Examiner*—Mitchell J. Shein
*Attorney, Agent, or Firm*—Henry W. Collins; George H. Gerstman

[57] ABSTRACT

An analog data transmission circuit for a biomedical implant employs a linear amplifier to modulate the impedance of a resonant circuit tuned to an externally generated constant carrier frequency. The resonant circuit comprises a tuned coil in circuit with a linear modulating switch and a digital modulating switch. The digital switch is gated by the digital data output from digital control circuitry within the implant. The linear amplifier output drives the linear modulation switch. The switches are preferably matched pairs of MOSFET's of opposite polarity having complementary parasitic diodes which form a phantom diode bridge. The bridge acts as a full wave rectifier and boosts the bias voltage on the sources of the FET pair forming the linear modulation switch such that the radiated amplitude is independent of the distance of the programming head. A timed power-up circuit supplies power to the amplifier and starts a square wave calibration period in response to the approach of the programming head. For ICEG transmission, a charge dump circuit depolarizes the lead before it is coupled to the amplifier.

5 Claims, 3 Drawing Figures

ANALOG TELEMETRY SYSTEM FOR BIOMEDICAL IMPLANT

BACKGROUND OF THE INVENTION

The invention relates generally to biomedical implant telemetry systems for analog physiological data and more particularly to intracardiac waveform transmission from an implanted cardiac pacer.

For many years fully implanted tissue stimulators have been used to treat cardiac and nervous disorders. Microelectronic circuits inside a hermetically sealed implanted case generate electrical impulses according to a prescribed set of parameters. By far the most common species of this type of implant is the cardiac pacer. A sealed battery powered pulse generator is connected to an insulated electrical conductor which passes into and through the vascular system and terminates in an electrode which is attached inside the heart, for example, to the bottom of the right ventricle. Electrical impulses generated by the sealed circuitry are applied via this lead, ordinarily using a metal case of the pulse generator as a ground electrode. If the stimulation pulse is correctly timed and exceeds a so called capture threshold, the ventricle will contract in response to the electrical stimulation. The same lead is employed as an electrical sensor to detect naturally generated electrical impulses which characterize spontaneous cardiac activity to inhibit artificial stimulation to avoid competition with the natural heart rhythm.

It is now commonplace to prescribe changes to the stimulation pulse parameters and other criteria by externally transmitting coded signals to the implanted circuitry. The first commercially successful type of inbound data transmission used electromagnetic impulse programming to rapidly actuate a tiny reed switch connected to a counter chain. Pulse width modulation systems have evolved based on improved electromagnetic impulse programming as well as RF signalling.

Outbound telemetry systems have recently been introduced to allow two-way communication between the external programmer and the implant. One of the most severe restrictions on outbound telemetry systems is power consumption. Battery operated pacers are designed to remain implanted for five to ten years. A conventional transmitter inserted in the pacer would consume too much power if used for any significant length of time. To overcome this limitation, resonant reflected signal transponder-like systems have been proposed in which the carrier frequency is supplied externally and modulated internally by the implant. Impedance modulated resonant transponder circuit systems are shown in U.S. Pat. No. 4,361,153 assigned to the assignee of the present invention and incorporated herein by reference. U.S. Pat. No. 4,361,153 discloses an outbound telemetry system which allows transmission of information from the implanted device while consuming a minimum amount of power. This telemetry system includes a resonant impedance modulated transponder in the implant which modulates the phase of the carrier in accordance with a pulse width modulated binary signal representative of the condition of the parameter registers in the implant. In this way, when interrogated, the pacer can inform the physician of the current programmed values of the various programmable parameters. U.S. Pat. No. 4,223,679 to Schulman purports to disclose an impedance reflecting resonant circuit apparently relying on frequency modulation of the carrier.

In addition to digitally stored parameter data, stored programs (software) and the like, it would be desirable to have a means for transmitting out of the pacer certain measured or sensed variables which are analog in nature. Two of the most interesting variable quantities are battery voltage and electrical amplitude of natural activity on the cardiac lead. Absent stimulation, the lead acts as an electrical pickup and electrical signals of varying amplitude appear on the lead. If the lead is attached to the inside of the heart, the resulting signal is known as an intracardiac electrogram or ICEG signal. It is desirable to obtain an ICEG since it is a different, and in some cases, a better means of studying the electrophysiology of the heart. Electrophysiological studies of the heart are extremely important in diagnosing and treating certain arrhythmias. The ICEG cannot be duplicated externally by a conventional EKG. It is, however, extremely difficult to reliably transmit the ICEG signal given the battery power constraints of the pacer. Analog to digital conversion of the ICEG signal would be ideal given the proper sampling rate because of the inherent fidelity of the signal. However, A/D converters consume excessive power. Analog transmission on the other hand presents the problem of base line calibration and possible distortion which would not necessarily be present in the A/D conversion option.

One of the items of interest for an ICEG transmitter would be the ability to inspect the ICEG signal immediately following the application of an artificial stimulation pulse to see whether capture had occurred. This aim is frustrated by the retention on the lead of a decaying charge after the stimulation pulse which can mask natural electrocardiac activity.

SUMMARY OF THE INVENTION

Accordingly, the general object of the invention is to transmit a reliable high fidelity analog signal from the implant without excessive power consumption. A correlary object is to provide a means for calibrating external recording equipment and minimizing the effect of drift and changes in the orientation of the external receiver relative to the implant. Another goal of the invention is to enable real-time external reception of the ICEG signal immediately following a stimulation pulse to evaluate capture threshold.

These and other objects of the invention are achieved by the novel outbound telemetry system of the present invention. The analog telemetry system builds upon the foundation of the digital transmission system described in U.S. Pat. No. 4,361,153. The tuned coil and pair of MOSFET's remains dedicated to transmission of purely digital information. Another pair of MOSFET's of the opposite type (n or p-channel) biased to a linear region is connected in circuit with the tuned coil. The two pairs of MOSFET's form complementary analog and digital switches which are used at mutually exclusive times for transmitting either analog or digital information. The analog switches are modulated by the output of a linear amplifier which is connected to the cardiac lead via an analog transmission gate controlled by the programmable digital command circuitry of the implant. The tuned coil is also connected in parallel to a power-up circuit. Following an initial delay, the power-up circuit connects power to the normally dormant linear amplifier and initiates a timed calibration cycle which superimposes on the amplifier output a binary signal of known dimensions to allow external calibration. Following the calibration mode, the ICEG signal is applied to the input of the amplifier and the amplifier output linearly modulates the impedance of the tuned coil which causes a corresponding linear variation in the phase relationship of the reradiated signal. A charge dump circuit automatically depolarizes the lead immediately following the stimulation pulse so that the ICEG signal can be transmitted accurately. This system has the notable advantage of utilizing the same external and internal circuitry for analog as well as digital transmission.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
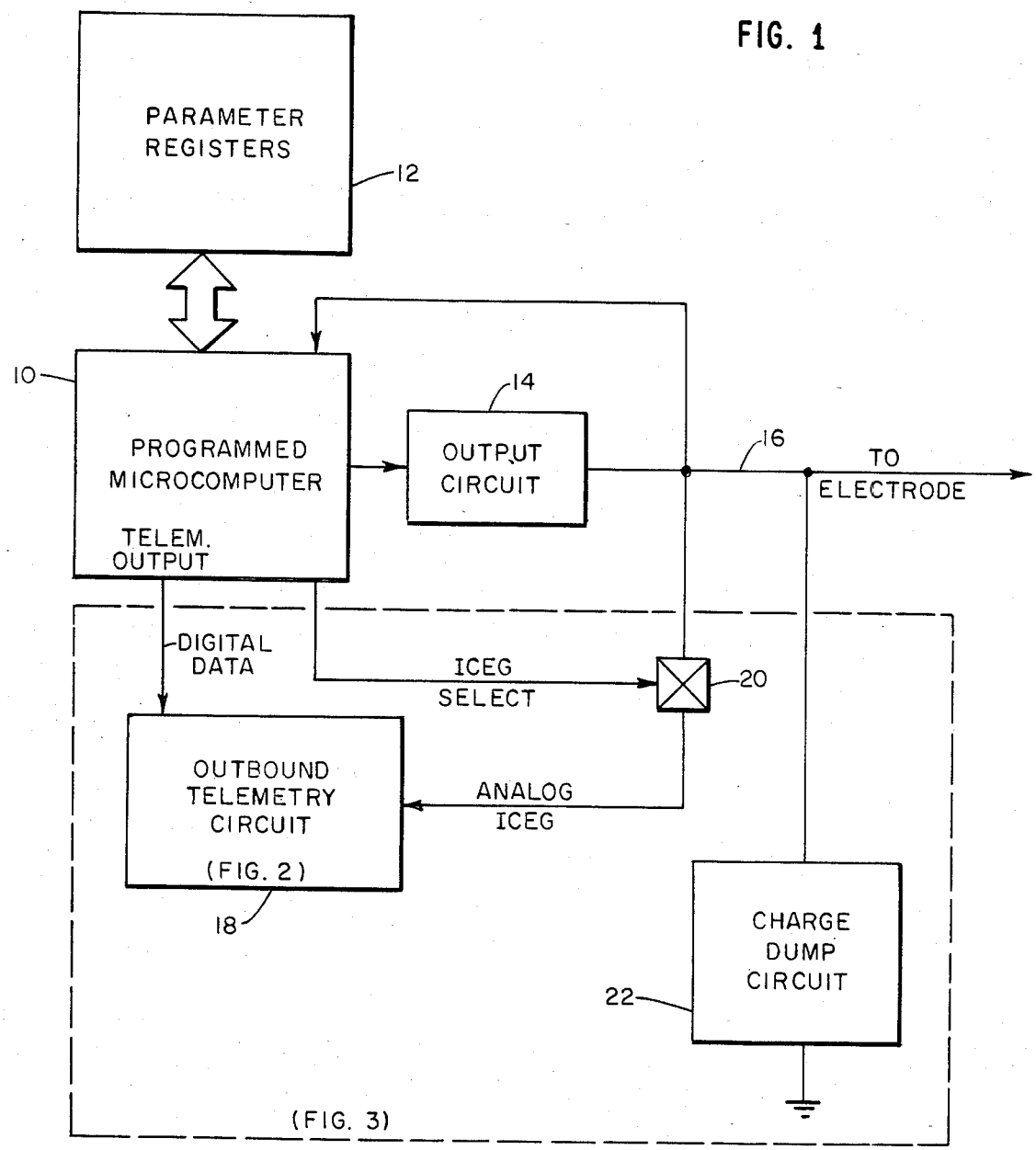
FIG. 1 is a block diagram of an implanted cardiac pacer which includes the outbound telemetry system of the present invention.

The outbound telemetry system of the present invention is best understood in conjunction with an implanted cardiac pacer, a part of which is shown in the block diagram of FIG. 1. This pacer includes a programmed microcomputer 10 and a number of parameter registers 12 which store values used by the pacer, such as the pulse rate, the pulse width, the pulse amplitude, the refractory period and other relevant parameters. The information stored in the parameter registers 12 is used by the microcomputer 10 in conjunction with the sensed signals to determine when the heart needs to be stimulated. When such stimulation is required, the microcomputer sends a signal to an output circuit 14 which in turn applies a stimulation pulse through the lead 16 connected to an electrode attached inside the heart.

The microcomputer also provides digital data to a telemetry circuit 18. See, for example, U.S. application Ser. No. 195,665, filed Oct. 9, 1980 by Lesnick entitled "Implantable Externally Programmable Microprocessor-Controlled Tissue Stimulator", which is assigned to the assignee of the present application and is incorporated herein by reference. The same telemetry circuit 18 also receives a dynamically varying analog intracardiac electrogram (ICEG) signal from the lead 16 which is attached to the electrode. An ICEG select signal from the microcomputer gates the ICEG signal via analog switch (transmission gate) 20 to the telemetry circuit. Also attached to the lead 16 is a charge-dump or depolarization circuit 22 which will remove any residual decaying charge which might remain on the lead 16 after a stimulation pulse has been applied to the heart.

Figure 2:
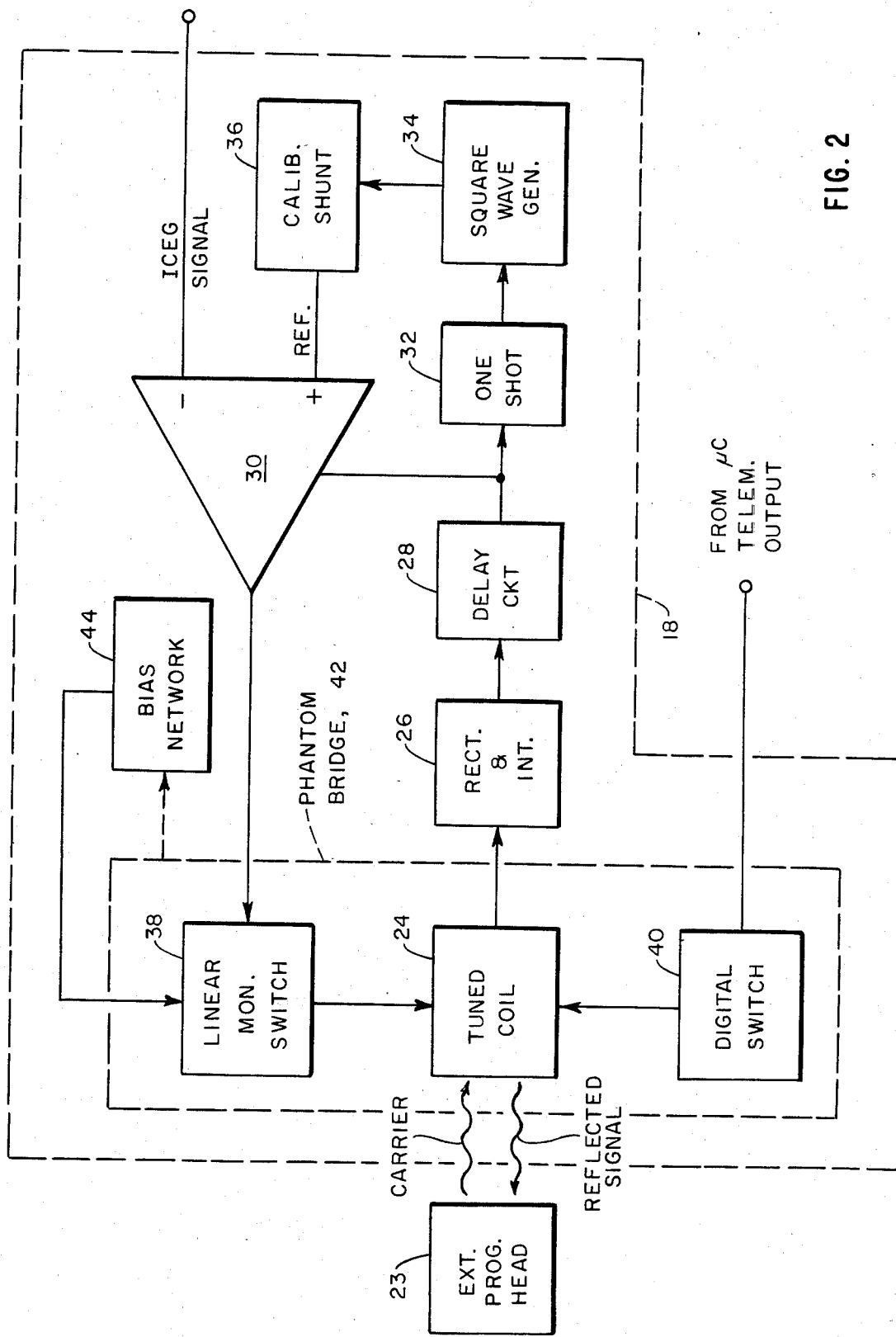
FIG. 2 is a block diagram of the outbound telemetry system for the implanted cardiac pacer shown in FIG. 1.
Figure 3:
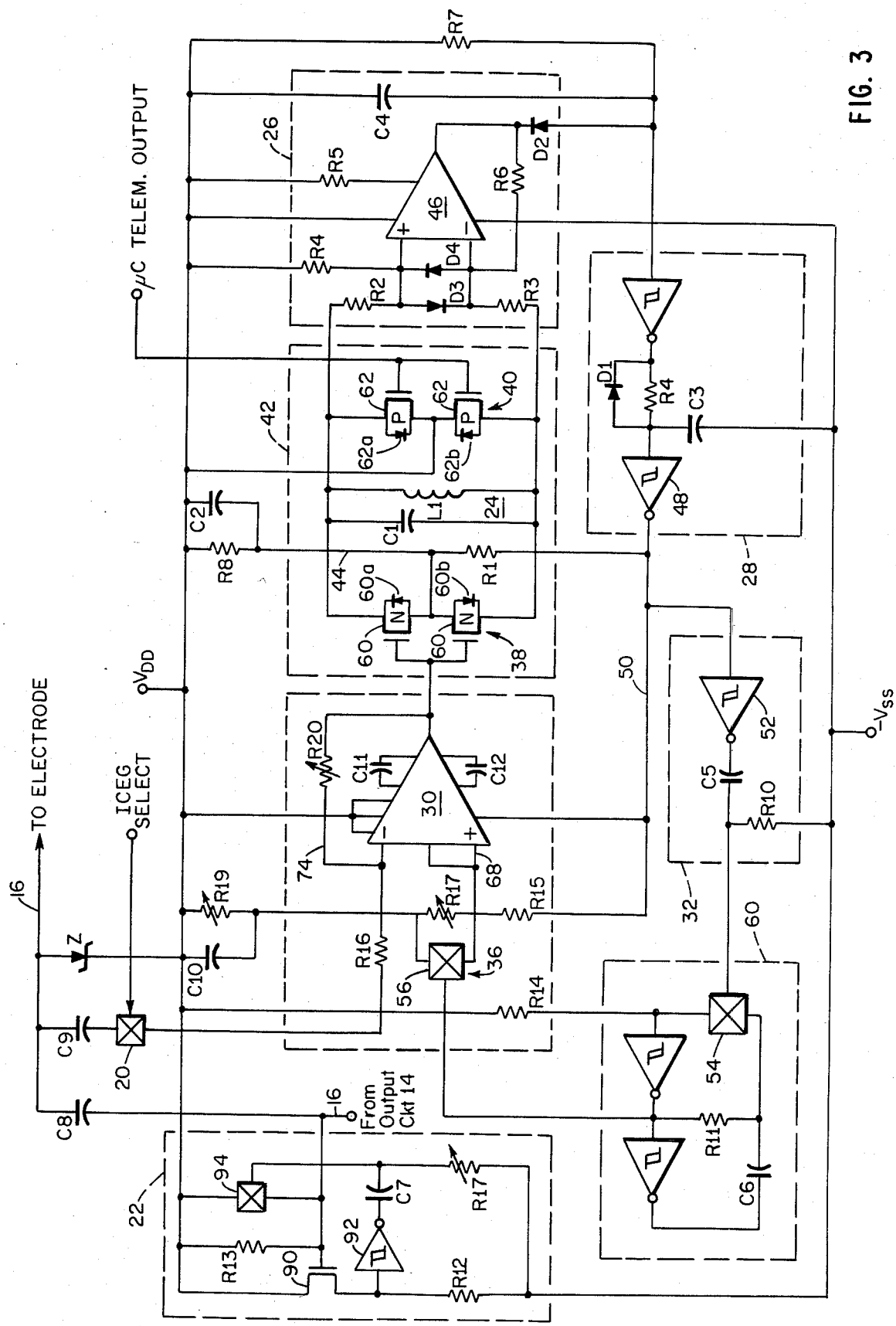
FIG. 3 is a schematic diagram of the circuitry of the outbound telemetry system for the implanted cardiac pacer of FIG. 1.

The outbound telemetry system of the present invention is more specifically shown in FIGS. 2 and 3. This telemetry system is activated by a programming head 23 (FIG. 2) located outside the body corresponding to head 10 in U.S. Pat. No. 4,361,155. Activation of the telemetry system occurs when the programming head is moved close to the body near the location of the implant containing the outbound telemetry circuitry. The programming head includes a carrier transmitter which transmits a continuous wave electrical output at a constant frequency low enough to achieve magnetic coupling with the coil 24 whose resonant or bandpass frequency is centered at the carrier frequency. The oscillating magnetic field which is generated by the programming head thus radiates into the implant and induces a corresponding voltage in the tuned coil 24 which in turn reradiates a secondary magnetic field at the same carrier frequency. The reradiated or reflected signal is received by the head 23. As described in U.S. Pat. No. 4,361,153, the modulation signal is recovered by a phase shift detector. The recovered analog voltage level is the output denoted "delta phi" ($\Delta\phi$) in FIGS. 12 and 14 of U.S. Pat. No. 4,361,153.

As shown in FIG. 2, the tuned coil 24 is connected to a rectifier and integrator circuit 26 which triggers a delay circuit 28 when sufficient power is coupled into the tuned coil from the external programming head. After a brief delay, the linear amplifier 30 is activated and a one-shot circuit 32 is triggered to apply a square wave output from generator 34 to a calibration shunt 36 for a predetermined calibration mode period. Calibration shunt circuit 36 is connected to the reference input of linear amplifier 30. The other input to the amplifier is connected via analog switch 20 (FIG. 1) to the lead 16 to obtain the ICEG signal. The output of the linear amplifier 30 is applied to linear modulation switch 38 to modulate the impedance of the tuned coil 24. Alternatively, digital data from the microcomputer 10 can be supplied to modulate a digital switch 40 connected in parallel to the tuned coil 24. The pairs of MOSFET's which make up the complementary switches 38 and 40 have parasitic diodes correctly oriented to form a phantom bridge 42 which acts a full wave rectifier to supplement a bias network 44 which compensates the linear switch 38 for variations in the level of energy coupled into the tuned coil from the programming head 23.

As shown in FIG. 3, the tuned coil 24 includes coil L1 connected in parallel with capacitor C1. The voltage induced by the carrier signal in the tuned coil 24 is applied to a rectifier and integrator circuit 26 to detect a minimum coupling level. Inititally, the signal in the rectifier circuit passes through limiting diodes D3 and D4 which cut off excess highs and lows thereby feeding an amplitude-limited or chopped AC signal to a high-gain, stable operational amplifier 46. The output of the amplifier 46 is fed to half-wave recitifying diode D2 which removes negative excursions from the signal. The resulting DC pulses are accumulated by integrating capacitor C4. If adequate coupling persists, this accumulated signal eventually attains a threshold necessary to trigger delay circuit 28 which powers up the remainder of the circuit. The power-up is not immediate, however, since a turn-on delay is built into the circuit 28. One reason for the delay is to avoid the effects of any electro-magnetic interference which might provide a surge of power. Capacitor C3 charges gradually to a voltage level of $V_{DD}$, the system ground level. The delay is about 1/10 of a second and following the delay Schmitt trigger 48 causes line 50 which is normally $V_{DD}$ to go to $V_{SS}$, negative supply voltage nominally −4.2 volts (two lithium cells). The constant $V_{SS}$ output of Schmitt trigger 48 powers the various elements of the circuit as will be described below.

The output of the delay circuit 28 triggers one-shot 32 which times the self-calibration cycle which lasts for about 8 seconds. Schmitt trigger 52 converts the $V_{SS}$ input to $V_{DD}$ thereby causing capacitor C5 to charge up. As the capacitor C5 discharges, a voltage is provided to the square-wave generator 60 through transmission gate 54. This voltage powers the square-wave generator 34 which generates a square-wave signal which is used to calibrate the received signal. This voltage is sufficient to power the square wave generator only while the discharged voltage remains above a predetermined threshold. It has been determined that approximately 8 seconds is a sufficient time interval to adequately calibrate the circuit. Therefore, capacitor C5 and resistor R10 should be chosen so that the discharge time is about 10 seconds (figuring that around the last couple of seconds the discharged voltage is below the driving threshold).

The output of the square-wave generator 34, preferably 40 Hz, is fed to the control input of transmission gate 56 which is normally open. Gate 56 operates as the calibration shunt 36 (FIG. 2). The application of the square-wave signal causes the gate 56 to oscillate between open and closed states. While the gate 56 is closed, resistor R18 is shunted and when gate 56 is open, an open circuit appears across the gate. Resistor R18 is a part of the series voltage divider formed by R15, R18 and R19. The opening and closing of the gate 56 results in a varying voltage being applied to the non-inverting input of linear amplifier 30. Amplifier 30 is preferably a commutating auto zeroing operational amplifier (CAZ op amp) to avoid offset drift.

The inverting input of amplifier 30 is connected to the lead 16 via resistor R19, transmission gate 20 and decoupling capacitor C9.

When gate 20 is closed, the output of amplifier 30 provides an input voltage representing the signal on the lead 16 to the gates of a pair of N-channel field effect transistors (FETs) 60. A pair of P-channel FET's 62, connected in parallel with the N-channel FET's 60, is used for digital transmission. Each of the FET's 60 and 62 also has a parasitic diode connected between the source and drain. The two pairs of parasitic diodes 60a and 62a form a "phantom" full wave bridge rectifier 42.

The N-channel FET's 60 differ from the P-channel FET's 62 in that the N-channel FET's 60 are biased into their linear operating region while the sources of the P-channel FET's 62 are grounded, i.e. the P-channel FET's 62 are either totally on or totally off. A voltage divider supplies the source bias network 44 for the N-channel FET's 60 to operate in their linear modulation region. Preferably network 44 biases the FET's 60 to the center of their linear range. However, the bias voltage is not necessarily constant; it is affected by the power coupled into the tuned coil in the following manner. The voltage divider is connected to the bridge 42 which adds or subtracts its rectified voltage to the constant voltage divider output to provide a variable supplementary bias component. For example, if R1 and R8 are equal, their junction will be at $-2.1$ volts. If the rectified voltage were 0.1 volts, it would supplement the constant voltage making it less negative. The arrangement as shown in FIG. 3 is such that the more power coupled into the tuned coil by the external carrier, the lower the modulation amplitude from the N-channel FET's. The gain of amplifier 30 is selected so that the peaks in the amplified ICEG signal do not exceed the linear range of the FET's.

The charge-dump circuit 22 of the outbound telemetry system of the present invention removes any residual charge which might remain on the lead 16 after a stimulation pulse has been applied to the heart. In order to remove the charge, the lead is grounded for a short interval of time. As shown in FIG. 3, after the current passing through the FET 90 reaches a predetermined level, a Schmitt trigger 92 forces normally open analog switch 94 to close thereby grounding lead 16 via capacitor C8. The time required for removing the charge from the electrode lead is approximately fifty milliseconds. This capability for removing the charge from the electrode enables the telemetry system of the present invention to determine whether capture has been achieved following a stimulation pulse.

The following table provides representative values and specifications for the components of the circuit of FIG. 3. These specifications merely serve as an example of one embodiment of circuitry for carrying out the invention in a specific application. Other embodiments may, of course, have substantially different specifications, yet still be within the scope of the invention.

TABLE

| | |
|---|---|
| R1 | 100 Kilohms |
| R2 | 22 Kilohms |
| R3 | 22 Kilohms |
| R4 | 5.6 Megohms |
| R5 | 22 Megohms |
| R6 | 5.6 Megohms |
| R7 | 10 Megohms |
| R8 | 100 Kilohms |
| R9 | 10 Megohms |
| R10 | 10 Megohms |
| R11 | 5.6 Megohms |
| R12 | 10 Megohms |
| R13 | 50 Kilohms |
| R14 | 10 Megohms |
| R15 | 1 Megohm |
| R16 | 50 Kilohms |
| R17 | variable |
| R18 | 5 Kilohms |
| R19 | 1 Megohm |
| R20 | 1 Megohm |
| C1 | .022 Microfarad |
| C2 | 1 Microfarad |
| C3 | .01 Microfarad |
| C4 | .11 Microfarad |
| C5 | 1 Microfarad |
| C6 | .01 Microfarad |
| C7 | .01 Microfarad |
| C8 | 10 Microfarads |
| C9 | 6.8 Microfarads |
| C10 | .22 Microfarad |
| C11 | .01 Microfarad |
| C12 | .01 Microfarad |
| Op Amp 38 | LM 3078 |
| Op Amp 30 | ICL 7601, gain of 20 |

In operation, when properly located, the programming head 23 couples voltage into the tuned coil 24 in the implant which eventually actuates the delay circuit 28. Following a momentary delay, the self calibration mode automatically begins. Resistor R18 is varied in relation to the other resistances R15 and R19 in the reference voltage divider such that the difference at the noninverting input of amplifier 30 between the unshunted and shunted conditions caused by square-wave modulation of analog gate 56 amounts to a known value, for example, 4 or 5 millivolts. A strip chart recorder (not shown), for example, connected to the output of the phase shift detector in the programming head 23 (see FIGS. 12 and 14 of U.S. Pat. No. 4,361,155) will record two levels which will be known to vary by 4 or 5 millivolts to allow the transverse axis of the strip chart recorder to be calibrated.

Following the start-up mode including the self calibration period, the microcomputer circuit 10 latches the gate 20 closed via the ICEG select line. The waveform on the lead 16 is amplified by linear amplifier 30 and used to modulate the impedance of the tuned coil circuit via the N channel FET's. Meanwhile, the P channel FET's used only for digital transmission are in the quiescent mode; but for the effect of the parasitic diodes 62a, they represent an open circuit. However, the phantom bridge created by the parasitic diodes 60a and 62a, supplements the bias network which biases the sources of the N channel FET's 60 to perform an automatic gain control. Additional power induced in the tuned circuit from the programming head reduces the modulation effect of the N channel FET's 60 to maintain the amplitude of the waveform superimposed on the carrier at a constant level independent of the proximity of the programming head in relation to the implant.

If desired, the normal pacing mode can continue to operate in the presence of the programming head. When a stimulation pulse is generated by the output circuit 14 (FIG. 1), the ICEG transmission gate 20 is momentarily opened. Following the stimulation pulse, the charge dump circuit 22 depolarizes the lead and the lead is reconnected to the ICEG amplifier 30 via gate 20. In this way, the waveform following stimulation can be analyzed to see whether capture has been obtained.

The advantages of the invention lie in its inherent simplicity and duality of function. Without altering the digital telemetry system, the present invention adds to the tuned circuit transponder an analog capability which exploits an incidental feature of the existing digital telemetry system to enhance the fidelity of the analog transmitted signal. The complementary symmetry of the P channel and N channel FET's allows the parisitic diodes to coact as a phantom full wave rectifier bridge to use the coupled external power as an auxiliary bias voltage supply for automatic gain control of the superimposed waveform signal. The result is a reproducible, linear, highly accurate signal which allows ICEG waveforms recorded at different times to be compared for diagnosis. Moreover, the square wave self-calibration signal allows the strip chart recorder or oscilloscope to be calibrated so that an approximate measurement in the signal level in millivolts on the lead 16 can be obtained in real time. All of this is done with extremely low cost to the power budget constraints imposed by the vital battery capacity of the pacer power supply. The quiescent current drain from the dormant circuitry is on the order of 1 microampere.

Although described in conjunction with cardiac pacers and ICEG transmission, the analog telemetry system herein is adaptable to other types of implants and various analog signals. As various changes can be made in the above constructions without departing from the scope of the invention; it should be understood that all matter contained in the above description or shown in the accompanying drawings shall be interpreted as illustrative and not in a limiting sense, the scope of the invention being indicated by the appended claims and all equivalents thereto.

What is claimed is:

1. An implant analog telemetry system comprising
a fully implantable biomedical device including a tuned coil circuit with a tuned coil and transistor means in circuit therewith having a linear operating region for altering the impedance of said tuned circuit as a function of an applied control input, and an external telemetry receiver including means for generating a constant frequency carrier at the tuned frequency of said coil, and receiver means for producing an output varying in response to the phase shift between the externally generated carrier and the received signal due to the reflected signal from said tuned coil circuit, said implanted device further including a linear amplifier having an input connected to said transistor means as the control signal, and means for supplying a variable bias voltage to said transistor means as a function of the level of energy coupled into said tuned coiled circuit from said external telemetry receiver, said variable bias means including means for supplying a nominally fixed bias to said transistor means corresponding to the middle of said linear operating region and means for rectifying the signal coupled into the tuned coil circuit due to said carrier frequency and combining the rectified signal with said fixed bias to provide a supplemental variable bias component which creates an inverse relationship with the coupling level, whereby variations in the proximity or strength of the coupled carrier signal have a reduced effect on the amplitude of the recovered waveform at the output of said receiver means.

2. An implant analog telemetry system, comprising
a fully implantable biomedical device including a tuned coil circuit with a tuned coil and transistor means in circuit therewith having a linear operating region for altering the impedance of said tuned coil circuit as a function of an applied control signal, and a linear amplifier having an input connected to receive an analog signal to be transmitted and an output connected to said transistor means as the control signal, and an external telemetry receiver including means for generating a constant frequency carrier at the tuned frequency of said coil and receiver means for producing an output varying in response to the phase shift between the externally generated carrier and the received signal reflected by said tuned coil circuit, said implantable device further including means responsive to a predetermined level of coupling of the carrier signal into the tuned coil circuit for supplying power to said linear amplifier, said power supplying means including means for rectifying and accumulating the signal induced by said carrier in said tuned coil circuit, and said power supplying means further including means responsive to the attaining of a predetermined level by said accumulated signal for supplying power to said amplifier following a predetermined additional delay.

3. An implant analog telemetry system, comprising
a fully implantable biomedical device including a tuned coil circuit with a tuned coil and transistor means in circuit therewith having a linear operating region for altering the impedance of said tuned coil circuit as a function of an applied control signal, and a linear amplifier having an input connected to receive an analog signal to be transmitted and an output connected to said transistor means as the control signal, and an external telemetry receiver including means for generating a constant frequency carrier at the tuned frequency of said coil and receiver means for producing an output varying in response to the phase shift between the externally generated carrier and the received signal reflected by said tuned coil circuit, said implantable device further including means responsive to a predetermined level of coupling of the carrier signal into the tuned coil circuit for supplying power to said linear amplifier, said implantable device further including a self calibration circuit responsive to the supplying of power to said amplifier means for applying for a predetermined calibration period an input signal to said amplifier signal which alternates between two levels by a predetermined known value, whereby the recovered output of said receiver means can be calibrated by observing the difference between said two levels and noting that said difference corresponds to the known value.

4. An implant analog telemetry system, comprising a fully implantable biomedical device including a tuned coil circuit with a tuned coil and transistor means in circuit therewith having a linear operating region for altering the impedance of said tuned coil circuit as a function of an applied control signal, and a linear amplifier having an input adapted to be connected to a varying electrical signal and an output connected to said transistor means as the control signal, and an external receiver including means for generating a constant frequency carrier at the tuned frequency of said coil circuit and receiver means for producing an output varying as the phase shift between the externally generated carrier and the received signal due to the signal reflected by said tuned coil circuit, said implantable device further including means for generating and applying a fixed bias voltage to said transistor means to bias said transistor means toward the middle of its linear operating region, and full wave rectifying diode bridge means connected to said tuned coil circuit for supplying rectified variable power due to the coupling level of said carrier frequency to said bias voltage to provide a supplemental variable component to compensate for variations in the level of coupling.

5. A cardiac pacer/ICEG telemetry system, comprising a fully implantable cardiac pacer including conductor means making electrical contact with the heart, means for generating and applying electrical stimulation pulses to the heart via said conductor means, a tuned coil circuit including a tuned coil and transistor means in circuit therewith having a linear operating region for altering the impedance of said tuned coil circuit as a function of an applied input signal, a linear amplifier having an input and an output connected to said transistor means as the control signal, and analog switch means for coupling said amplifier input to said conductor means on command to feed the natural ICEG signal appearing on said conductor means through said amplifier, and an external telemetry receiver including means for generating a constant frequency carrier at the tuned frequency of said coil and receiver means for producing an output varying as the phase shift between the externally generated carrier and the received signal due to the signal reflected from said tuned coil circuit, said cardiac pacer further including automatic means for momentarily grounding said conductor means following the application of a stimulation pulse and means for closing said analog switch means immediately following the grounding of said conducting means, whereby residual charge decaying on said conductor means is removed in order to observe the ICEG signal immediately following stimulation to evaluate the capture threshold.

* * * * *